United States Patent
Johnsen et al.

(10) Patent No.: US 10,231,815 B2
(45) Date of Patent: Mar. 19, 2019

(54) SPIRAL BIRD'S NEST FILTER

(71) Applicant: Cook Medical Technologies LLC, Bloomington, IN (US)

(72) Inventors: Jeppe Dufresne Johnsen, Froerup (DK); Jens Kold, Kokkedal (DK); Rasmus Boje Vendelbo Juliussen, Soeborg (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 370 days.

(21) Appl. No.: 14/992,184

(22) Filed: Jan. 11, 2016

(65) Prior Publication Data
US 2016/0206418 A1 Jul. 21, 2016

Related U.S. Application Data

(60) Provisional application No. 62/104,334, filed on Jan. 16, 2015.

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2002/018* (2013.01); *A61F 2210/0014* (2013.01); *A61F 2230/0091* (2013.01)

(58) Field of Classification Search
CPC .......... A61F 2002/018; A61F 2002/011; A61F 2/01; A61F 2/00; A61F 2/02; A61F 2002/016; A61F 2210/0014; A61F 2230/0091
See application file for complete search history.

(56) References Cited

U.S. PATENT DOCUMENTS

| | | | |
|---|---|---|---|
| 6,019,779 A | 2/2000 | Thorud et al. | |
| 7,094,249 B1* | 8/2006 | Broome | A61B 17/221 606/200 |
| 7,976,561 B2 | 7/2011 | Bruckheimer et al. | |
| 8,226,679 B2* | 7/2012 | Johnson | A61F 2/01 210/435 |
| 2006/0020285 A1 | 1/2006 | Niermann | |
| 2007/0112372 A1 | 5/2007 | Sosnowski et al. | |
| 2013/0226291 A1 | 8/2013 | Pavcnik et al. | |

FOREIGN PATENT DOCUMENTS

EP 2893902 A1 * 7/2015 ............... A61F 2/01

OTHER PUBLICATIONS

Cardinal Search Report dated Aug. 13, 2014.

* cited by examiner

*Primary Examiner* — Todd Scherbel
*Assistant Examiner* — Brooke Labranche
(74) *Attorney, Agent, or Firm* — Brinks Gilson & Lione (57) ABSTRACT

The disclosure provides for a spiral filter and delivery apparatus where the filter comprises a support supporting a body and defining a frame. The frame comprises a proximal end extending to a distal end. A filtering member may be attached to the proximal end and extend distally to the distal end. The filtering member and the frame may move between a delivery state and a deployed state. In the deployed state, the frame extends helically within the circumference of the body vessel and has a filtering lumen formed therethrough. The filtering member may be disposed within the filtering lumen in a spiral for filtering within the intended body vessel.

20 Claims, 7 Drawing Sheets

SPIRAL BIRD'S NEST FILTER

CROSS-REFERENCE TO RELATED APPLICATIONS

This application claims the benefit of priority under 35 U.S.C. § 119(a) to U.S. Provisional Application No. 62/104,334, filed Jan. 16, 2015 all of which are hereby incorporated by reference in their entirety.

FIELD

The present disclosure relates to medical devices. More particularly, the disclosure relates to a spiral vena cava filter and delivery apparatus.

BACKGROUND

Physicians often use vascular implantable devices to treat various conditions. Such devices may be designed to be inserted in tubular body vessels, such as arteries and veins. Such devices may exert a radial force against the vessel wall. If the radial force is insufficient, the device may migrate in the vasculature. However, over time a strong radial force may cause unintended consequences to the vessel wall. This may be particularly problematic in highly flexible body vessels, such as in the vena cava.

In addition, after the vascular implantable device is in the body for a sufficient time it may become endothelialized within the vessel tissue, making it more difficult to remove.

BRIEF SUMMARY

The present disclosure provides generally for a spiral vena cava filter device and delivery apparatus. This medical device may be arranged in a body vessel having a vessel wall. The vessel wall has a circumference about a longitudinal axis. The device may have a support comprising a first member having a first end and extending to a second end. The support further has a second member having a third end and extending to a fourth end. The first end may be attached to the third end at a first joint and the second end may be attached to the fourth end at a second joint, defining an area about which the first and second members are disposed.

The device further may have a body attached to the support and extending about the area. The support and the body may define a frame. The frame may have a proximal end and extend to a distal end. In addition, the device may have a filtering member having a first portion attached to the first joint and extending distally to a second portion. The second portion may be attached to the second joint.

The frame and the filtering member may have a delivery state and a deployed state. In the deployed state, the frame may extend helically within the body vessel and have a filter lumen formed therethrough such that the filtering member is disposed within the filter lumen and comprises a spiral for filtering within the body vessel.

The first member may have a first curve and the second member comprises a second curve in the delivery state. The first and second curves may be S-shaped. The first member may be a first wire and the second member may be a second wire. The first member may have a first length and the second member may have a second length wherein the first length is the same as or substantially the same as the second length. The filter member may have a filter length being substantially the same as or greater than the first length.

The body may comprise a fabric or a membrane. The membrane may contain polyethylene, such as Dyneema®. The body may have an outer side arranged to contact the vessel wall and an inner side opposite from the outer side. The body may further be disposed about the support. The frame may helically extend for about one to about two circumferential rotations about the longitudinal axis when in the deployed state.

This disclosure also provides for a medical assembly, having the device discussed herein and a delivery apparatus. In one embodiment, the delivery apparatus may contain an outer sheath having an outer member extending from a proximal part and to a distal part, the outer member being tubular and forming a sheath lumen extending therethrough.

The apparatus may further comprise an inner member having a proximal inner portion and extending distally to a distal inner portion. The inner member may be slidably disposed within the sheath lumen wherein the distal inner portion moves the device out of the sheath lumen and into the body vessel for filtration.

In another embodiment, the delivery apparatus may have an inner sheath having a sheath member extending from a first part to a second part, the sheath member being tubular and forming a sheath lumen extending therethrough. The second part may be removably coupled to a third part distal the second part. The delivery apparatus may also have an elongate member comprising a proximal portion extending distally from the first part to a distal portion being attached to the third part. The elongate member may be slidably disposed in the sheath lumen to move the device from the delivery state to the deployed or treatment state.

The delivery apparatus further may have a first gripper attached to the second part and being removably coupled to the first joint and a second gripper distal the first gripper and attached to the third part, the second gripper being removably coupled to the second joint. The grippers may be coupled to the device in the delivery state and decoupled from the device in the deployed state. The grippers may each have an open state and a closed state to removeably couple to the joints, respectively.

As one possible advantage, the frame provides a structure with a sufficient surface to exert a radial force against the vessel wall. This surface allows for uniform distribution of such radial force on the vessel wall. This distribution may avoid possible unintended consequences against the vessel wall.

In addition, the frame is structured without any holes or apertures. Such structure reduces the risk of endothelialization by the body vessel tissue while implanted. This may facilitate retrieval.

The present disclosure may be better understood by referencing the accompanying figures.

DETAILED DESCRIPTION

The present disclosure provides for a vena cava filter device for filtering in a body vessel and a delivery apparatus to deliver the device to the intended site. The materials, methods, figures, and examples disclosed herein are illustrative only and not intended to be limiting. The disclosed figures are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which said disclosure pertains. In the case of conflict, the present documents and definitions will control.

"Adjacent" referred to herein is nearby, near to, or in close proximity with.

The terms "proximal," "distal," and derivatives thereof will be understood in the frame of reference of a medical physician using a medical device; thus, proximal refers to those locations closer to the physician and distal refers to locations farther away from the physician (e.g. deeper in the patient's vasculature).

"Radially" and derivatives thereof will be understood to mean along the radial axis of the body vessel. Likewise, "radial force" and derivatives thereof will be understood to mean a force applied along the radial axis.

"Substantially" referred to herein means approximately, about, or close to.

Figure 1:
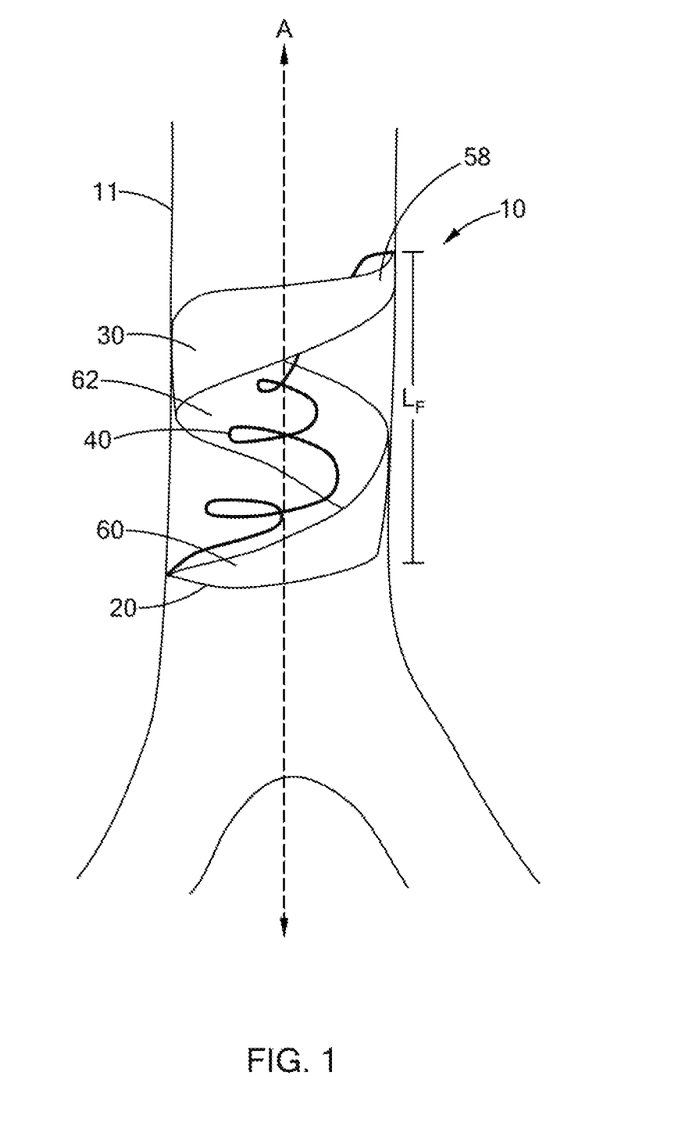
FIGS. 1 and 2 are environmental side views of a medical device in a deployed state for filtering in the body vessel in accordance of one embodiment of the present invention.

FIG. 1 illustrates an environmental view of the device 10 in the body vessel with vessel wall 11. The vessel wall 11 has a cross-sectional circumference about a longitudinal axis A. FIG. 1 shows the device 10 in its deployed state. In this embodiment, the device has a body 30 extending about a support 20. The body 30 and the support 20 may define a frame. The frame may have a length $L_F$ along the longitudinal axis A and a filter lumen 62 formed therethrough. The frame may extend from a proximal end 60 to a distal end 58 about the filter lumen 62. The device may also have a filtering member 40 attached to the frame.

The device 10 may be any size suitable for the intended application or body vessel. For example, to complement the vena cava, the device may have a diameter about 15 to about 30 millimeters. Likewise, the device may have a length of about 25 to about 50 millimeters, from the proximal end 60 to the distal end 58.

Further, the device may move between a delivery state for delivery to the intended filtering site and a deployed state for filtering within a body vessel. The device may be pre-set or biased to the deployed state such that it may be elongated or constrained in the delivery state and predisposed to the deployed state upon release. Such properties may be achieved through use of the material chosen for the device (e.g. Nitinol, discussed below). In the deployed state (shown in FIG. 1), the frame takes on a generally cylindrical shape to compliment the intended body vessel.

Figure 2:
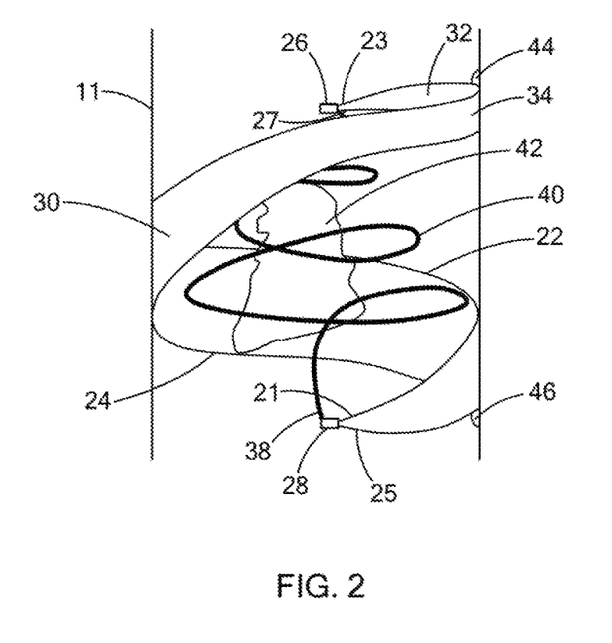

FIG. 2 depicts further details of the device in the deployed state, capturing a clot 42. In particular, the device includes the support having a first member 22 with a first end 21 extending to a second end 23 and a second member 24 having a third end 25 extending to a fourth end 27. The first end 21 may be attached to the third end 25 at a first joint 28. The second end 23 may be attached to the fourth end 27 at a second joint 26.

The joints may be formed by any means known in the art, including laser welding, mechanical joining, or crimping. The first and second members may define an area about which the first and second members (22 and 24, respectively) are disposed. In the deployed state (as shown in FIG. 2), the first and second members may run generally parallel or disposed along and in contact with the vessel wall until they join at the first and second joints.

The device further may have a body 30 attached to the support and extending about the area, defining a frame. In addition, the device may have a filtering member 40 having a first portion 38 attached to the first joint 28 and extending distally to a second portion 36 (obscured in FIG. 2, but shown in FIG. 4). The second portion 36 may be attached to the second joint 26. The frame and the filtering member 40 may have a delivery state and a deployed state as discussed herein.

The device may optionally have barbs to prevent device migration during filtration. For example, the proximal end may have a first barb 46 and the distal end may have a second barb 44 to engage the vessel wall 11. A skilled artisan will understand that the device may be formed with no barbs, one barb, or two barbs. In addition, the barbs may be moved along the frame to any position suitable for the intended purpose to engage the vessel wall.

In the deployed state, the frame may extend helically within the body vessel and have a filter lumen formed therethrough such that the filtering member 40 is disposed within the filter lumen and comprises a spiral for filtering within the body vessel.

Figure 3:
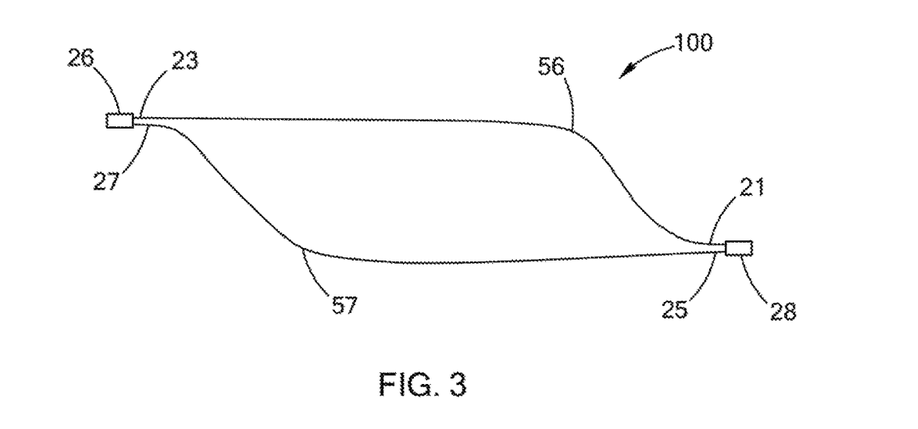
FIG. 3 is a side view of one embodiment of a frame of the device of FIG. 1.

Contrastingly, FIG. 3 illustrates the frame 100 in the delivery state. As depicted here, the first member has a first end 21 extending to a second end 23 and the second member extends from a third end 25 to a fourth end 27. The first end 21 may be attached to the third end 25 at a first joint 28. Likewise, the second end 23 may be attached to the fourth end 27 at a second joint 26. In one embodiment, the first member comprises a first curve 56 and the second member comprises a second curve 57 in the delivery state. In one embodiment the first and second curves (56 and 57, respectively) are substantially S-shaped (as shown in FIG. 3).

Figure 4:
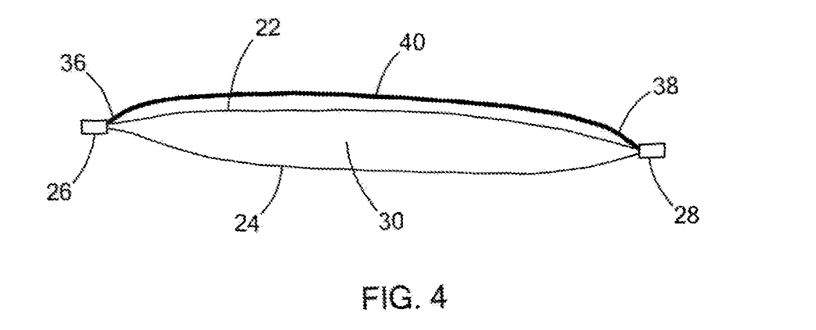
FIG. 4 is a side view of one embodiment of the device of FIG. 1.

FIG. 4 also illustrates the device in a delivery state, now containing the filtering member. In one embodiment, the first member 22 may comprise a first wire and the second member 24 may comprise a second wire. The first and second wires may comprise Nitinol.

Nitinol is a metal alloy of nickel and titanium having a unique shape memory setting property and being biocompatible. At a transition temperature, Nitinol may undergo a phase change from Martensitic to Austenite, changing its structure. Here, the support could be heat set or pre-set to the deployed state and maintained in the delivery state (shown in FIG. 4) until deployed. In addition to this phase changing ability, Nitinol is also quite flexible.

The first member 22 may have a first length and a second member 24 may have a second length wherein the first length is substantially the same as the second length. In addition, the filtering member 40 may have a filter length. The filter length may be substantially the same as the first length. Alternatively, the filtering length may be greater than the first length or the second length. It will be understood that a larger or longer filtering member may give the device greater filtering capacity. The filtering member may also be made out of any suitable material for the intended application, including Nitinol.

The body 30 disposed about the area could be formed of any suitable material for its intended application to contact the vessel wall. In one embodiment, the body 30 comprises a fabric, such as a graft. In another embodiment, the body 30 comprises a membrane. The membrane may comprise polyethylene. In particular, the membrane may comprise Dyneema®. Dyneema® is a lightweight, high strength, flexible polyethylene fiber that is biocompatible and may be used for medical implants.

The body 30 may be attached to the support through any means known in the art including gluing, stitching, or bonding. In one embodiment, the body could partially or completely surround or be disposed about the support. In a preferred embodiment, the body may be mounted on or over the support to be free of holes or apertures between the body and the support. This may provide for no or reduced ingrowth of the vessel wall tissue about the frame, facilitating withdrawal.

Figure 5:
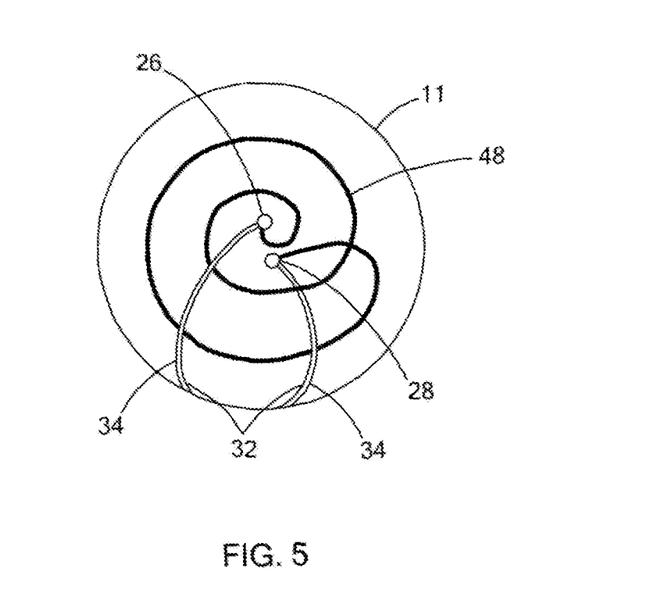
FIG. 5 is an end view of one embodiment of the device of FIG. 1.

When forming the frame, it may extend helically for about one to about two circumferential rotations about the longitudinal axis of the vessel wall when the device is in the deployed state. This arrangement is depicted in FIG. 5, which shows an end view of the device within the body vessel 11. This view illustrates the second joint 26 and the first joint 28 deeper into the page from the second joint 26. In one embodiment, the body 30 may comprise an outer side 34 arranged to contact the vessel wall 11 and an inner side 32 opposite from the outer side 34. This device may evenly distribute radial force against the vessel wall, avoiding any particular points of high radial force. In addition, this end view shows that the filtering member may be formed of the spiral 48. The spiral may facilitate good filtering capacity.

Figure 6A:
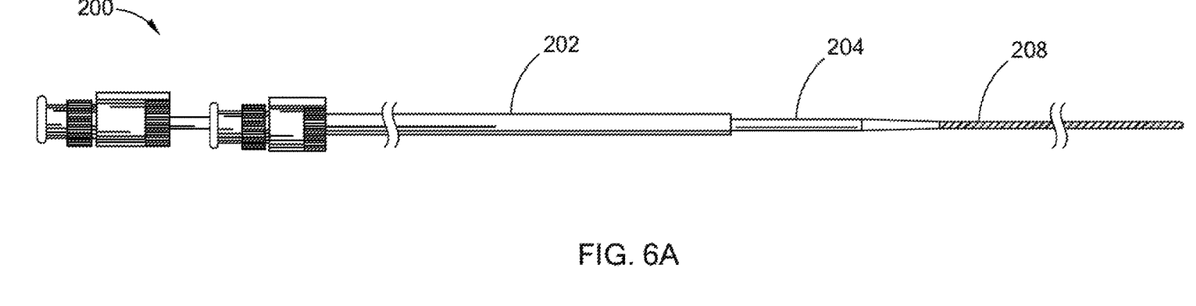
FIGS. 6A-6B is a delivery apparatus for introducing the device of FIG. 1.
Figure 6B:
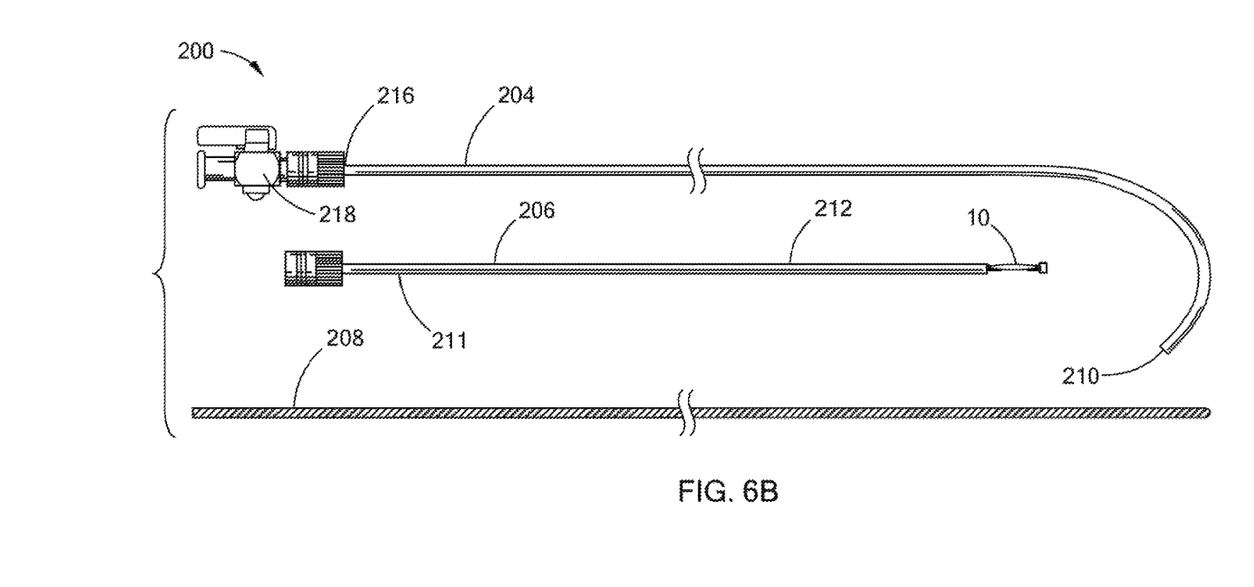

FIGS. 6A-B generally depicts a delivery apparatus for the device as discussed herein. Further details of the delivery apparatus will be discussed in FIGS. 7-9. In FIGS. 6A-B, the device 10 may be delivered or retrieved by way of the Seldinger technique. As shown, the delivery apparatus 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner sheath or inner catheter 206 to be percutaneously inserted to a desired location in the body vessel. The inner sheath may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end or part 216 to a distal end or part 210, the body being tubular and including a sheath lumen extending therethrough.

As shown, the apparatus 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device may also be used to expand the access site.

When the distal end 210 of the outer sheath 204 is at the desired location in the body vessel, the wire guide 208 is removed and the device 10, having a proximal segment contacting a distal or second part 212 of the inner sheath 206, is inserted into the outer sheath 204. The inner sheath 206 is advanced through the outer sheath 204 for deployment of the device 10 through the distal end 210 to treat the body vessel. The catheter 206 extends from a proximal portion or first part 211 to the second part 212 and is configured for axial movement relative to the outer sheath 204.

In this example, the second part 212 is shown adjacent to the device. Thus, before deployment, the device 10 is coaxially disposed within the lumen of the outer sheath 204 and removably coupled to the second part 212 of the catheter 206, or in the alternative, the device 10 is merely pushed by, but not coupled to, the second part 212 of the catheter 206.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner sheath 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end or distal part 210 of the outer sheath 204 adjacent the deployed device in the vasculature. The inner sheath 206 is advanced through the outer sheath 204 until the distal or second part 212 protrudes from the distal end 210 of the outer sheath 204. The second part 212 may be coupled to a proximal end of the device 10, after which the inner catheter 206 is retracted proximally, drawing the device 10 into the outer sheath 204.

Figure 7A:
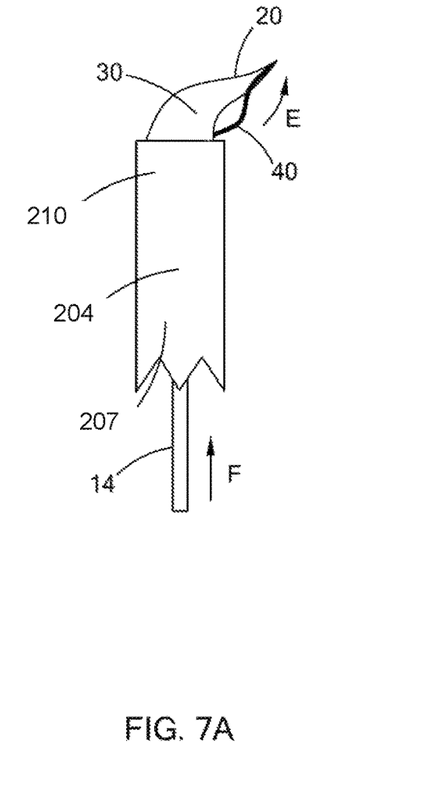
FIGS. 7A-7B depicts steps of deploying the device of FIG. 1 in accordance with one embodiment of the present invention.
Figure 7B:
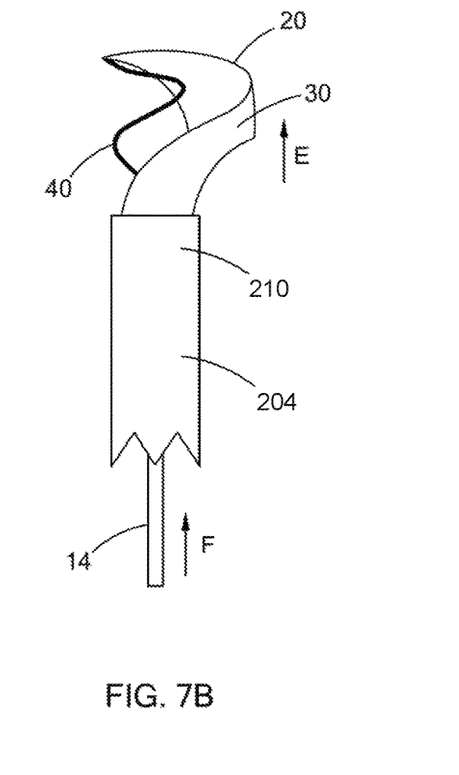

FIGS. 7A-B depict further details of the steps of one delivery method. In this embodiment, the medical assembly comprises the device as described herein and the delivery apparatus having an outer sheath 204 with an outer member extending from a proximal part (not shown) to a distal part 210. The outer member may be tubular and forming a sheath lumen 207 extending therethrough.

The delivery apparatus further comprises the inner member 14 having a proximal inner portion extending distally to a distal inner portion. The distal inner portion may be contained within the outer sheath 204. The inner member 14 may be slidably disposed within the sheath lumen 207 wherein the distal inner portion moves the device out of the sheath lumen 207 and into the body vessel for filtration. FIG. 7A depicts the device exiting the outer sheath 204 where the support 20, body 30, and filtering member 40 are exiting at arrow E based on a force applied at arrow F to the inner member 14. As the force is applied, the device moves further out of the sheath lumen 207 as shown in FIG. 7B. It will be understood that the force could also withdraw the outer sheath 204 for the device to exit the delivery apparatus.

In this embodiment, the assembly may not have an inner sheath 206 (shown in FIGS. 6A-B). The inner member 14 may move through the outer sheath 204. Alternatively, the inner member 14 may be the inner sheath 206 shown in FIGS. 6A-B.

Alternatively, the device may be delivered using a delivery apparatus containing an elongate member with a pair of grippers. Such alternative delivery is described in the flow diagram in FIG. 8. In step 90, the physician may couple the device to the delivery apparatus in the delivery state. In step 92, the physician may dispose the device in the body vessel. In step 94, the physician may slide an elongate member to move the device from the delivery state to the deployed state. In step 96, the physician may uncouple the device from the delivery apparatus. In step 98, the physician may withdraw the delivery apparatus from the body vessel.

Figure 8:
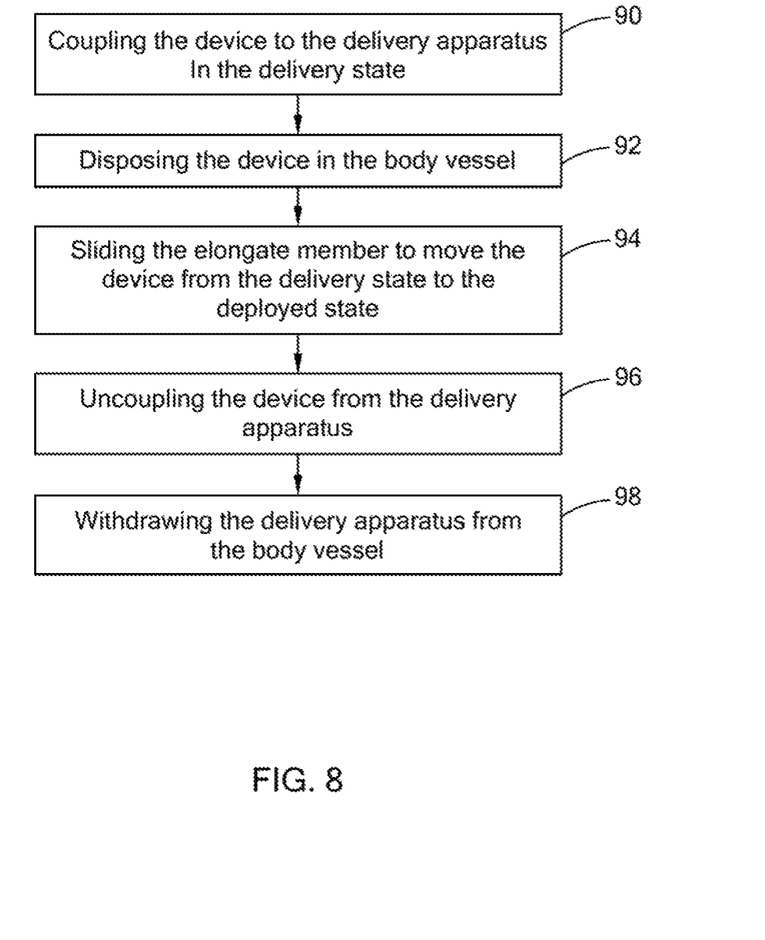
FIG. 8 is a flow diagram of steps of deploying the device of FIG. 1 in accordance with one embodiment of the present invention.
Figure 9A:
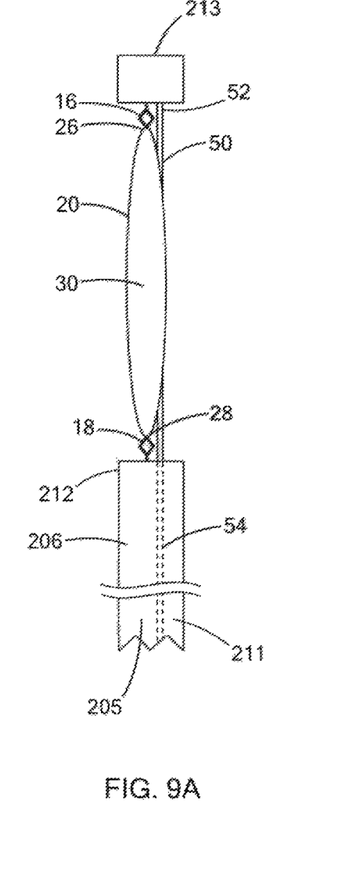
FIGS. 9A-C depicts steps of the method of FIG. 8.
Figure 9B:
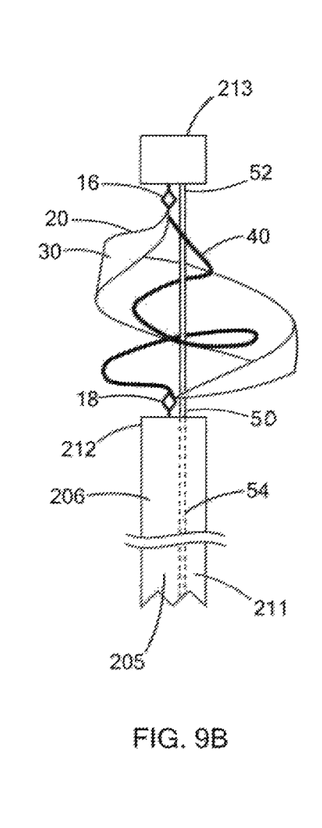
Figure 9C:
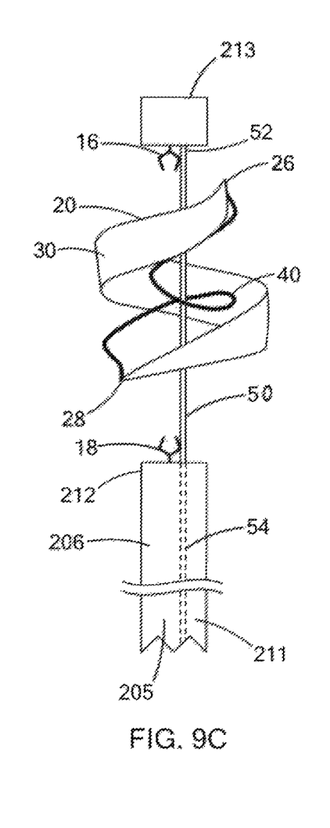

FIGS. 9A-C depicts the steps of the flow diagram of FIG. 8. For example in FIG. 9A, the delivery apparatus may comprise the inner sheath 206 having a sheath member extending from a first part 211 to a second part 212. The sheath member may be tubular and forming a sheath lumen 205 extending therethrough. The second part 212 may be removably coupled to a third part 213 distal the second part 212.

The delivery apparatus may further comprise an elongate member 50 comprising a proximal portion 54 extending distally from the first part 211 to a distal portion 52 being attached to the third part 213. The elongate member 50 may be slidably disposed in the sheath lumen 205 to move the device from the delivery state to the deployed state as shown in FIG. 9A and 9C, respectively.

The delivery apparatus may further comprise a first gripper 18 attached to the second part 212 and being removably coupled to the first joint 28. The device may comprise a second gripper 16 distal the first gripper 18 and attached to the third part 213. The second gripper 16 may be removebly coupled to the second joint 26. The grippers may be coupled to the device in the delivery state (FIG. 9A) and decoupled from the device in the deployed state (FIG. 9C).

The first gripper 18 may have a first open state and a first closed state to removably coupled to the first joint 28. Likewise, the second gripper 18 may have a second open state and a second close state to removably couple to the second joint 26. As shown in FIG. 9A, the device is delivered in the inner sheath or catheter 206 in the delivery state, elongated. Here, the body 30, support 20, and filtering member 40 are all maintained in the delivery state.

As the physician advances the device into the vascular to the site of filtration, the physician may slide the elongate member 50 proximal as shown in FIG. 9B. Sliding the elongate member 50 proximally may move the third portion 213 proximal and the device into an intermediate state where it is attached to the grippers in the deployed configuration.

In FIG. 9C, the first and second grippers (18 and 16, respectively) may move to their open states and release the first and second joints (28 and 26, respectively). In this Figure, the device is moved into its deployed state and is no longer attached to the delivery apparatus. The support 20, body 30, and filtering member 40 are now in the deployed state. They may exert a radial force against the vessel wall and the delivery apparatus may be withdrawn from the body vessel.

The apparatus described above is merely one example of an assembly that may be used to deploy the device in a body vessel. Of course, other apparatus, assemblies and systems may be used to deploy any embodiment of the device without falling beyond the scope or spirit of the present invention.

While the present invention has been described in terms of certain preferred embodiments it will be understood that the invention is not limited to these disclosed embodiments as those skilled in the art may make various modifications without departing from the scope of the following claims.

The invention claimed is:

1. A medical device for filtering in a body vessel, the body vessel having a vessel wall and forming a longitudinal axis, the device comprising: a support comprising a first member having a first end and extending to a second end, the support comprising a second member having a third end and extending to a fourth end, the first end being attached to the third end at a first joint and the second end being attached to the fourth end at a second joint, defining an area about which the first and second members are disposed; a body attached to the support and extending about the area, the support and the body defining a frame, the frame comprising a proximal end and extending to a distal end; and a filtering member having a first portion attached to the first joint and extending distally to a second portion, the second portion attached to the second joint, the frame and the filtering member having a delivery state and a deployed state, in the deployed state the frame extending helically within the body vessel and having a filter lumen formed therethrough such that the filtering member is disposed within the filter lumen and comprises a spiral for filtering within the body vessel, wherein the first member and the second member run generally parallel to each other from the first joint to the second joint in the deployed state.

2. The device of claim 1 wherein the first member comprises a first curve and the second member comprises a second curve in the delivery state.

3. The device of claim 1 wherein the device is pre-set to the deployed state.

4. The device of claim 1 wherein the first member comprises a first wire and the second member comprises a second wire.

5. The device of claim 4 wherein the first and second wires comprise Nitinol.

6. The device of claim 1 wherein the first member has a first length and the second member has a second length wherein the first length is substantially the same as the second length.

7. The device of claim 6 wherein the filtering member has a filter length, the filter length being greater than or substantially the same as the first length.

8. The device of claim 7 wherein the filter length is greater than the first length.

9. The device of claim 1 wherein the body comprises a fabric.

10. The device of claim 1 wherein the body comprises a membrane.

11. The device of claim 10 wherein the membrane comprises polyethylene.

12. The device of claim 10 wherein the membrane comprises biocompatible polyethylene fiber.

13. The device of claim 1 wherein the body comprises an outer side arranged to contact the vessel wall and an inner side opposite from the outer side.

14. The device of claim 1 wherein the body is disposed about the support.

15. The device of claim 1 wherein the frame helically extends for about one to about two circumferential rotations about the longitudinal axis when in the deployed state.

16. The device of claim 1 wherein the proximal end comprises a first barb and the distal end comprises a second barb to engage the vessel wall.

17. A medical assembly for filtering in a body vessel, the body vessel having a vessel wall and forming a longitudinal axis, the assembly comprising: a medical device comprising: a support comprising a first member having a first end and extending to a second end defining a length, the support comprising a second member having a third end and extending to a fourth end, the first end being attached to the third end at a first joint and the second end being attached to the fourth end at a second joint, defining an area about which the first and second members are disposed; a body attached to the support and extending about the area, the support and the body defining a frame, the frame comprising a proximal end and extending to a distal end; and a filtering member having a first portion attached to the first joint and extending distally to a second portion, the second portion attached to the second joint, the frame and the filtering member having a delivery state and a deployed state, in the deployed state the frame extending helically within the body vessel and having a filter lumen formed therethrough such that the filtering member is disposed within the filter lumen and comprises a spiral for filtering within the body vessel; wherein the first member and the second member run generally parallel to each other along the length in the deployed state, and a delivery apparatus comprising: an outer sheath having an outer member extending from a proximal part and to a distal part, the outer member being tubular and forming a sheath lumen extending therethrough; and an inner member having a proximal inner portion and extending distally to a distal inner portion, the inner member slidably disposed within the sheath lumen wherein the distal inner portion moves the medical device out of the sheath lumen and into the body vessel for filtration.

18. A medical assembly for filtering in a body vessel, the body vessel having a vessel wall and forming a longitudinal axis, the assembly comprising:
  a medical device comprising:
    a support comprising a first member having a first end and extending to a second end, the support comprising a second member having a third end and extending to a fourth end, the first end being attached to the third end at a first joint and the second end being attached to the fourth end at a second joint, defining an area about which the first and second members are disposed;
    a body attached to the support and extending about the area, the support and the body defining a frame, the frame comprising a proximal end and extending to a distal end; and
    a filtering member having a first portion attached to the first joint and extending distally to a second portion, the second portion attached to the second joint, the frame and the filtering member having a delivery state and a deployed state, in the deployed state the frame extending helically within the body vessel and having a filter lumen formed therethrough such that the filtering member is disposed within the filter lumen and comprises a spiral for filtering within the body vessel; and
  a delivery apparatus comprising:
    an inner sheath having a sheath member extending from a first part to a second part, the sheath member being tubular and forming a sheath lumen extending therethrough, the second part removably coupled to a third part distal the second part;
    an elongate member comprising a proximal portion extending distally from the first part to a distal portion being attached to the third part, the elongate member being slidably disposed in the sheath lumen to move the medical device from the delivery state to the deployed state;
    a first gripper attached to the second part and being removably coupled to the first joint; and
    a second gripper distal the first gripper and attached to the third part, the second gripper being removably coupled to the second joint, the grippers being coupled to the medical device in the delivery state and decoupled from the medical device in the deployed state.

19. The medical assembly of claim 18 wherein the first gripper has a first open state and a first closed state to removably couple to the first joint.

20. The medical assembly of claim 19 wherein the second gripper has a second open state and a second closed state to removably couple to the second joint.

* * * * *